US012580047B2

(12) United States Patent     (10) Patent No.:   US 12,580,047 B2

Ezrielev et al.     (45) Date of Patent:   *Mar. 17, 2026

(54) BIOLOGICAL SEQUENCE COMPRESSION USING SEQUENCE ALIGNMENT

(71) Applicant: Dell Products L.P., Round Rock, TX (US)

(72) Inventors: Ofir Ezrielev, Be'er Sheba (IL); Ilan Buyum, Kfar-Aza, IL (US); Jehuda Shemer, Kfar Saba (IL)

(73) Assignee: Dell Products L.P., Round Rock, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/658,925

(22) Filed: Apr. 12, 2022

(65) Prior Publication Data

US 2023/0230659 A1    Jul. 20, 2023

Related U.S. Application Data

(63) Continuation-in-part of application No. 17/648,193, filed on Jan. 18, 2022.

(51) Int. Cl.
    *G16B 30/20*       (2019.01)
    *G16B 50/30*       (2019.01)
    *G16B 50/50*       (2019.01)

(52) U.S. Cl.
    CPC ............. *G16B 30/20* (2019.02); *G16B 50/30* (2019.02); *G16B 50/50* (2019.02)

(58) Field of Classification Search
    CPC ........ G16B 30/20; G16B 50/30; G16B 50/50; G06F 16/1744
    See application file for complete search history.

(56) References Cited

U.S. PATENT DOCUMENTS

| | | | |
|---|---|---|---|
| 6,076,059 A | 6/2000 | Glickman et al. | |
| 6,363,381 B1 | 3/2002 | Lee et al. | |
| 6,537,773 B1 * | 3/2003 | Fraser ................... | C07K 14/30 |
| | | | 536/23.7 |

(Continued)

FOREIGN PATENT DOCUMENTS

| | | |
|---|---|---|
| CN | 107704617 A | 2/2018 |
| CN | 113760839 A | 12/2021 |

OTHER PUBLICATIONS

Thompson, Julie D., Toby J. Gibson, and Des G. Higgins. "Multiple sequence alignment using ClustalW and ClustalX." Current protocols in bioinformatics 1 (2003): 2-3.

(Continued)

*Primary Examiner* — Jensen Hu

(74) *Attorney, Agent, or Firm* — Workman Nydegger

(57)          ABSTRACT

Compressing files is disclosed. An DNA sequence to be compressed is first aligned. Aligning the DNA sequence includes splitting the DNA sequences into smaller sequences or portions that can be aligned. After the DNA sequence is spilt one or more time and aligned, a compression matrix is generated. Each row of the compression matrix corresponds to part of the DNA sequence. A consensus sequence is determined from the compression matrix. Using the consensus sequence, pointer pairs are generated. Each pointer pair identifies a subsequence of the consensus matrix. The compressed file includes the pointer pairs and the consensus sequence.

19 Claims, 10 Drawing Sheets

(56)                    References Cited

U.S. PATENT DOCUMENTS

| | | | |
|---|---|---|---|
| 6,700,513 B2 | 3/2004 | McGuire | |
| 9,678,973 B2 | 6/2017 | Trimble et al. | |
| 9,817,866 B1 | 11/2017 | Barrett et al. | |
| 10,268,544 B2 | 4/2019 | Anderson | |
| 10,423,341 B1* | 9/2019 | Kermani | G06F 3/0631 |
| 10,554,220 B1* | 2/2020 | Constantinescu | H03M 7/607 |
| 10,720,231 B1 | 7/2020 | Konerding et al. | |
| 10,777,304 B2 | 9/2020 | Baym et al. | |
| 11,669,526 B2 | 6/2023 | Master et al. | |
| 2001/0036271 A1 | 11/2001 | Javed | |
| 2003/0224384 A1 | 12/2003 | Sayood et al. | |
| 2008/0152235 A1 | 6/2008 | Bashyam et al. | |
| 2010/0033357 A1 | 2/2010 | Archbold et al. | |
| 2010/0257174 A1 | 10/2010 | Minuti | |
| 2011/0119240 A1 | 5/2011 | Shapira | |
| 2011/0219144 A1 | 9/2011 | Amit et al. | |
| 2011/0293605 A1 | 12/2011 | Sathish et al. | |
| 2013/0268206 A1 | 10/2013 | Porreca et al. | |
| 2013/0324417 A1* | 12/2013 | Kennedy | G16B 30/10 506/2 |
| 2014/0200166 A1* | 7/2014 | Van Rooyen | G16B 50/00 702/19 |
| 2015/0106345 A1 | 4/2015 | Trimble et al. | |
| 2015/0310219 A1 | 10/2015 | Haager et al. | |
| 2015/0331913 A1 | 11/2015 | Borowiec et al. | |
| 2016/0180019 A1 | 6/2016 | Van et al. | |
| 2016/0306794 A1 | 10/2016 | Huang et al. | |
| 2016/0306919 A1 | 10/2016 | Ding et al. | |
| 2016/0344849 A1* | 11/2016 | Thomas | G16B 30/20 |
| 2016/0364523 A1* | 12/2016 | Locke | G16B 30/10 |
| 2017/0052974 A1 | 2/2017 | Zackoski | |
| 2017/0058320 A1 | 3/2017 | Locke et al. | |
| 2017/0124254 A1 | 5/2017 | Van et al. | |
| 2017/0147226 A1 | 5/2017 | Oung et al. | |
| 2017/0357665 A1 | 12/2017 | Olivares-Amaya et al. | |
| 2018/0089369 A1* | 3/2018 | Semenyuk | G16B 50/00 |
| 2018/0349397 A1 | 12/2018 | Zaydman | |
| 2018/0364949 A1* | 12/2018 | Aston | G06F 3/067 |
| 2019/0050495 A1* | 2/2019 | Su | G06F 16/9017 |
| 2019/0065518 A1 | 2/2019 | Constantinescu et al. | |
| 2019/0214108 A1* | 7/2019 | Standley | G16B 40/00 |
| 2019/0318445 A1 | 10/2019 | Benthin et al. | |
| 2019/0371320 A1 | 12/2019 | Netzer | |
| 2020/0176076 A1* | 6/2020 | Heuckmann | G16B 20/20 |
| 2020/0226102 A1 | 7/2020 | Natanzon | |
| 2020/0364229 A1 | 11/2020 | Arcuri et al. | |
| 2021/0008128 A1 | 1/2021 | Nandakumar et al. | |
| 2021/0144226 A1 | 5/2021 | De Icaza Amozurrutia | |
| 2022/0374395 A1 | 11/2022 | Scrivano | |
| 2023/0229633 A1 | 7/2023 | Ezrielev et al. | |

OTHER PUBLICATIONS

Manikandan, P., and D. Ramyachitra. "Bacterial foraging optimization-genetic algorithm for multiple sequence alignment with multi-objectives." Scientific reports 7.1 (2017): 1-14.

Ceze, Luis, Jeff Nivala, and Karin Strauss. "Molecular digital data storage using DNA." Nature Reviews Genetics 20.8 (2019): 456-466.

Kumar, Manoj, et al. "Genetic algorithm: Review and application." Available at SSRN 3529843 (2010).

Particle swarm optimization, https://en.wikipedia.org/wiki/Particle_swarm_optimization, accessed as early as Jan. 2022.

Sievers, et al., Fast, scalable generation of high-quality protein multiple sequence alignments using Clustal Omega (Oct. 2011).

Wikipedia, Multiple sequence alignment; https://en.wikipedia.org/wiki/Multiple_sequence_alignment; retrieved Jan. 7, 2025.

https://en.wikipedia.org/wiki/Polysaccharide (accessed Jan. 14, 2025).

Joseph, et al, "Total Synthesis of Polysaccharides by Automated Glycan Assembly" pubs.acs.org/JACS 2020.

"Lapadula, Anthony J et al. "Congruent strategies for carbohydrate sequencing. 3. OSCAR: an algorithm for assigning oligosaccharide topology from MSn data." Analytical chemistry vol. 77, 19 (2005): 6271-9. doi: 10.1021/ac050726j" (Year: 2005).

Deorowicz, Sebastian, et al. "CoMSA: Compression of Protein Multiple Sequence Alignment Files." Bioinformatics, vol. 35, No. 2, Jul. 13, 2018, pp. 227-234, academic.oup.com/bioinformatics/article/35/2/227/5053318, https://doi. org/10.1093/bioinformatics/bty619. (Year: 2018).

Eduard Zorita, et al. Starcode: Sequence Clustering Based on All-Pairs Search. Vol. 31, No. 12, Jun. 15, 2015, pp. 1913-1919, https://doi.org/10.1093/bioinformatics/btv053. Accessed May 16, 2023. (Year: 2015).

Lee, Hui Sun et al. "GS-align forglycan structure alignment and similarity measurement." Bioinformatics (Oxford, England) vol. 31, 16 (2015): 2653-9. doi: 10.1093/bioinformatics/btv202 (Year: 2015).

Scholz, Karl W. "A Floppy Disk Operating System for the 8080 and Z80." Behavior Research Methods, vol. 10, No. 4, Jul. 1, 1978, pp. 527-530, https://doi.org/10.3758/bf03205340. Accessed Nov. 4, 2025. (Year: 1978).

* cited by examiner

1000

Storage Media
1008

UI Device
1010

Data Storage
1012

Memory
1002

NVRAM
1004

Processor
1006

Application(s)
1014

BIOLOGICAL SEQUENCE COMPRESSION USING SEQUENCE ALIGNMENT

FIELD OF THE INVENTION

Embodiments of the present invention generally relate to compression. More particularly, at least some embodiments of the invention relate to systems, hardware, software, computer-readable media, and methods for compressing data using multiple sequence alignment.

BACKGROUND

Data compression is a technology that provides numerous benefits. Compression reduces the size of the data by a compression ratio. By reducing the size of data, less storage space is required to store the data and less bandwidth is required to transmit compressed data.

BRIEF DESCRIPTION OF THE DRAWINGS

In order to describe the manner in which at least some of the advantages and features of the invention may be obtained, a more particular description of embodiments of the invention will be rendered by reference to specific embodiments thereof which are illustrated in the appended drawings. Understanding that these drawings depict only typical embodiments of the invention and are not therefore to be considered to be limiting of its scope, embodiments of the invention will be described and explained with additional specificity and detail through the use of the accompanying drawings, in which.

DETAILED DESCRIPTION OF SOME EXAMPLE EMBODIMENTS

Figure 1:
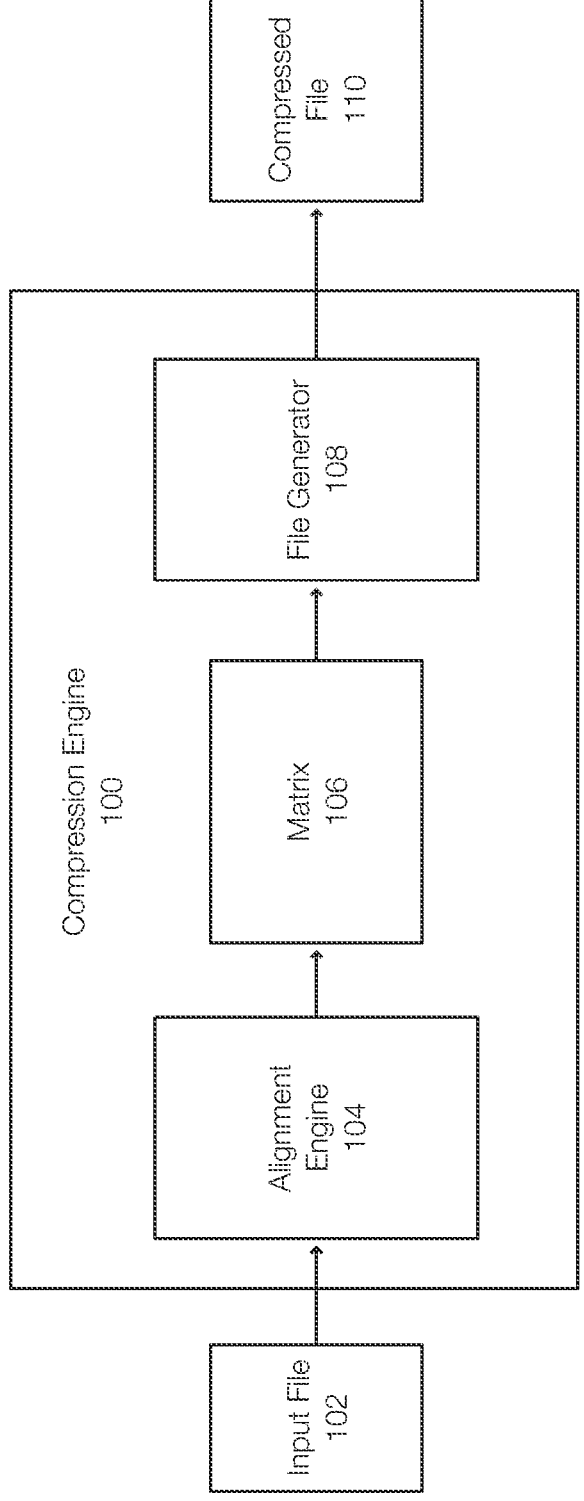
FIG. 1 discloses aspects of a compression engine configured to compress data.

Embodiments of the present invention generally relate to compression and compression operations using data alignment. More particularly, at least some embodiments of the invention relate to systems, hardware, software, computer-readable media, and methods for compressing data and further relate to compressing data using sequence alignment.

Embodiments of the invention provide a compression engine that is configured to compress data using an alignment mechanism. The compression engine receives a file as input and performs a splitting operation to generate a matrix of sequences. The file is split into multiple sequences. Each sequence corresponds to part of the file being compressed. When the matrix is generated, gaps may be included or inserted into some of the sequences for alignment purposes. Once the matrix is completed, a consensus sequence is identified or derived from the compression matrix. The original file is compressed by representing the input file as a list of pointer pairs into the consensus sequence. Each pointer pair corresponds to a part of the file and each pointer pair identifies the beginning and end of a subsequence in the consensus sequence. The file can be reconstructed by concatenating the subsequences in the consensus sequence identified by the pointer pairs.

Embodiments of the invention are discussed with reference to a file by way of example and not limitation. The compression operations discussed herein may be applied to any data or data type. Further, embodiment of the invention may be applied to large files such as disk/volume images or the like.

When compressing a file, one object of alignment is to divide the file into multiple pieces that are similar. The goal of alignment is to identify sequences that are similar. For example, the similarity of sequences can be scored. In a situation where n bits of a file are represented by a letter, a sequence of ABABAB may be similar to a sequence of ABAAAC. A similarity score may reflect, for example, how many of the letters match. In one example, similar sequences can be made to be identical by inserting gaps into the sequences. Identical, in this context, means that the columns of the sequences, when arranged in a matrix, have the same letters (or a gap).

More specifically, in order to achieve the alignment, it may be necessary to adjust some of the sequences such that each piece of the file includes data represented in a manner that allows the pieces or sequences to be aligned. For example, assume a file is represented by AAAAAAB. Also assume that the file is split into two pieces (or sequences): AAA and AAB. In order to align these sequences, it is necessary to insert a space or a gap. This may result in the following sequences (a space or gap is represented by "-"): AAA- and AA-B. When these sequences are aligned in a matrix, each column contains the same letter and/or gaps. This allows the file to be compressed as more fully described below.

The alignment process results in multiple sequences that can be arranged in a matrix in one example. Because a file may be large, the alignment process may involve an iterative process of splitting and aligning. This is performed until the length of the sequences is sufficient or when a consensus length has been reached.

By way of example, the alignment process maintains a list of pieces that can be split. These pieces may have the same length in one example. For each round or iteration, a piece is selected from that split. In an embodiment, a piece with the highest length is split, and aligned. If the consensus length is smaller by a determined threshold than the previous consensus length, new pieces or sequences resulting from the split are added back to the list of pieces that can be split. This process continues until resources are exhausted, the length of the consensus is sufficient (e.g., meets a threshold length), or the list of splitable pieces is empty. This process may also include adding spaces or gaps as appropriate. In one example, gaps are added in each alignment. When completed, a compression matrix is generated as discussed below.

FIG. 1 discloses aspects of compressing data with a compression engine. FIG. 1 illustrates a compression engine 100. The compression engine 100 may be implemented at the edge, at the near edge, or in the cloud and may include physical machines (e.g., servers), virtual machines, containers, processors, memory, other computing hardware, or the like or combination thereof. The compression engine 100 may cooperate with or be integrated with a system or application such as a data protection system. For example, data backups, volumes, disk/volume images, or the like may be compressed prior to transmission over a network, prior to storage, for archiving, or the like. In some examples, compression operations are examples of data protection operations.

The compression engine 100 is configured to receive a file 102 as input. The compression engine 100 outputs a compressed file 110. More specifically, the file 102 is received at an alignment engine 104 that is configured to generate a compression matrix 106. In one example, the alignment engine 104 may perform a greedy splitting algorithm on the file 102 to generate the matrix. The splitting algorithm, in effect, divides the bits of the file 102 into multiple sequences of the same length. After each split, the alignment of the pieces is evaluated. If not sufficiently aligned, one or more of the pieces may be split again. This process may continue until the remaining pieces of sequences are sufficiently aligned. Once aligned, the resulting sequences constitute the compression matrix 106 and each sequence may correspond to a row of the matrix 106. If necessary, gaps are inserted into some of the sequences such that the matrix 106 is aligned. Gaps may be inserted during the alignment process.

More specifically, the matrix 106 may be represented a structure that includes rows and columns. The alignment engine 104 may be configured to determine the number of columns and/or rows during the splitting or alignment operation. During alignment, the file 102 is split until the rows of the matrix 106 can be generated. The alignment performed by the alignment engine 104 ensures that, for a given column in the matrix 106, the entries are all the same, except that some of the entries in a given column may be gaps. As previously stated, during alignment, gaps may be inserted at various locations of the sequences such that each column contains the same information in each row or a gap.

A consensus sequence is identified from the matrix 106 or derived from the matrix 106 and used by the file generator 108 to generate the compressed file 110. The entire file 102 is represented in the consensus sequence. Because each of the rows correspond to a part of the file and each has information that is present in the consensus matrix, the bits in the file can be represented using pointers into the consensus sequence. The compressed file 110 may include the consensus sequence and the pointer pairs. Each row of the compression matrix may be represented by one or more pointers. Gaps in a given row are not represented by pointers. Once the compressed file 110 is generated, the compression matrix 106 may be discarded.

Figure 2:
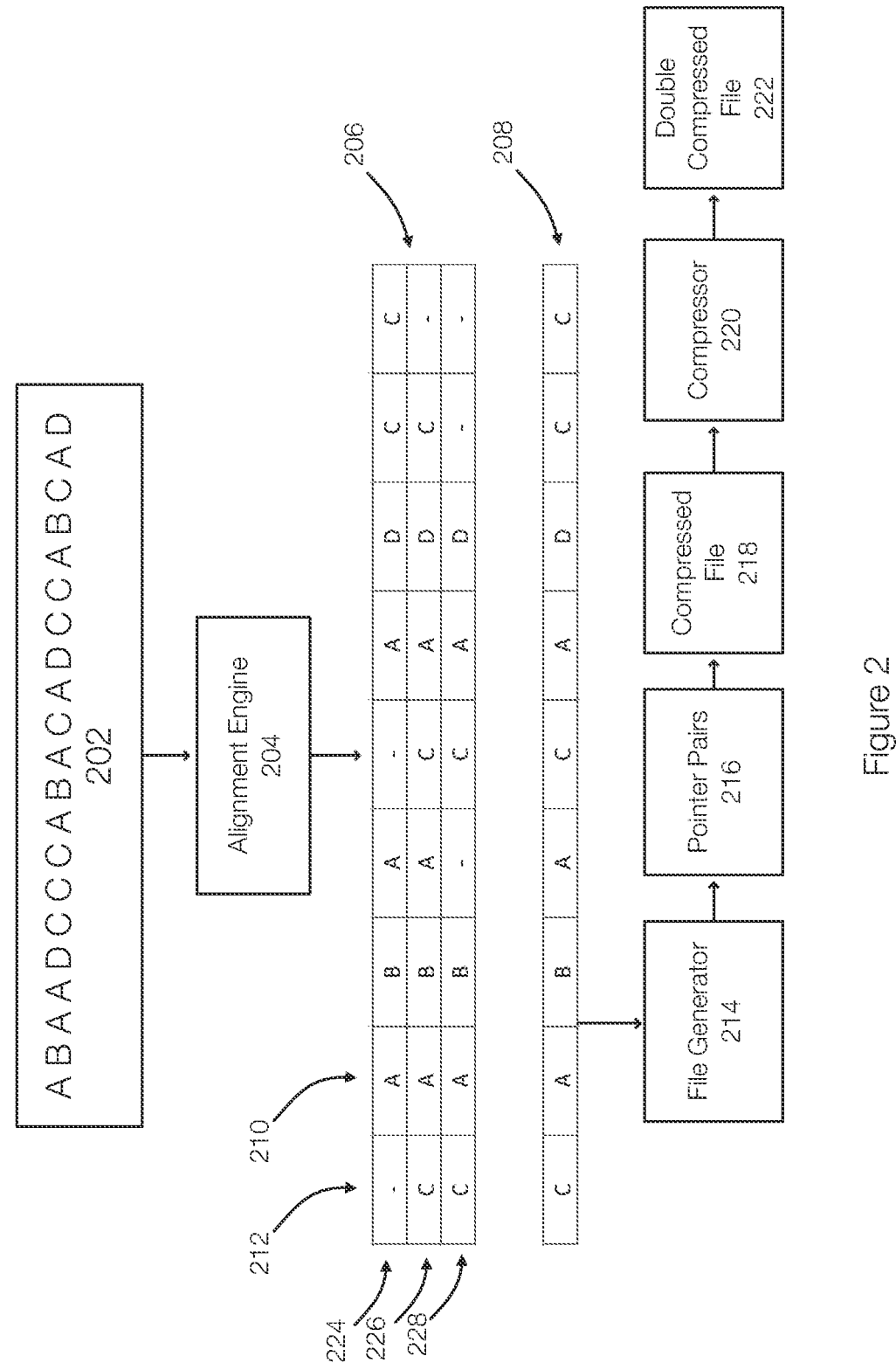
FIG. 2 discloses aspects of a compression engine configured to compress data using multiple sequence alignment.

FIG. 2 discloses aspects of compressing a file. In FIG. 2, a file 202 is illustrated or represented as a series of letters: ABAADCCCABACADCCABCAD. Each of these letters may represent n bits of the file 202. Because n may vary or change from one compression operation to the next compression operation, the compression ratio may also change. In one example, n may be specified as an input parameter to the alignment engine 204 or may be determined by the sequencing or aligning performed by the alignment engine 204. The size of n may impact computation time.

The file 202 is aligned (or sequenced) by the alignment engine 204 to generate a compression matrix 206. The compression matrix includes rows and columns. Each column, such as the columns 210 and 210, contain either the same letter and/or a gap, which gap is represented as a "-" in FIG. 2. During sequencing or alignment performed by the alignment engine 204, the file 202 may be split into pieces until the matrix 206 is generated. When the alignment engine 204 completes its work and the pieces of the input file 202 are aligned, each of the columns in the matrix 206 contains the same letter and/or a gap. Thus, each row of the matrix 206 of the column 212 include the letter "C" and a gap while the column 210 contains the letter "A" with no gaps. No mismatches (e.g., a column contains more than one letter) are allowed.

The alignment performed by the alignment engine 204 allows a consensus sequence 208 to be generated or determined. The consensus sequence 208 includes the letters of the corresponding columns from the matrix 206. In this example, the consensus sequence 208 is generated from the matrix 206. However, the matrix 206 may also include the consensus sequence 208.

In effect, the consensus sequence 208 is a vector v, where v[i] is the letter or letter type that exists in column i, disregarding gaps. The vector may be multi-dimensional when compressing multi-dimensional data.

The pseudocode performed by the alignment engine 204 is as follows:

```
input: file V, with each k bits represented as a single letter
set splitCandidates ←{V}
set nonSplit ←{ }
while |splitCandidates| > 0:
    baseCMSA ← CMSA(nonSplit ∪ splitCandidates)
    set splitCandidates_new ←{ }
    set nonSplit_new ← nonSplit
    for volumePiece in splitCandidates: //Can be done concurrently
        L,R ← halve volumePiece
        if len(CMSA(nonSplit ∪ splitCandidates\volumePiece ∪ L ∪ R)) <
len(baseCMSA):
            splitCandidates_new = splitCandidates_new ∪ L ∪ R
        else:
            nonSplit_new= nonSplit_new ∪ volumePiece
    splitCandidates = splitCandidates_new
    nonSplit = nonSplit_new
```

Once completed, the nonSplit sequences will be a matrix of letters and gaps, such as the matrix 206. The consensus sequence 208 is taken or derived from the matrix 206.

The file generator 214 uses the consensus matrix 208 to generate pointer pairs that represent the letter or bits in the file. In this example, the consensus matrix 208 is an array or vector with entries 0 . . . 8. When generating the pointer pairs, the matrix 206 may be processed row by row. In the first row, the first subsequence is ABA corresponds to locations 1, 2, and 3 of the consensus sequence 208. The first pointer in the list of pointer pairs 216 is thus $P_1$ (1:3).

Using the consensus matrix, the file 202 may be represented with the following pointer pairs 216, which each point into the consensus sequence 208 and correspond to a part of the file 202:
$P_1$-(1:3)—this corresponds to ABA (see row 224 of the matrix 206);
$P_2$-(5:8)—this corresponds to ADCC (see row 224 of the matrix 206);
$P_3$-(0:7)—this corresponds to CABACADC (see row 226 of the matrix 206);
$P_4$-(0:2)—this corresponds to CAB (see row 228 of the matrix 206); and
$P_5$-(4:6)—this corresponds to CAD (see row 228 of the matrix 206).

The compressed file 218 includes $P_1$ . . . $P_5$ and the consensus sequence 208. This information allows the file to be decompressed into the file 202. More specifically, the file

202 is reconstructed by replacing each pointer in the list of pointers with the subsequence (letters or bits corresponding to the letters) of the consensus sequence 208 to which the pointers point. This process does not require the gaps to be considered as the pointer pairs 216 do not reference gaps but only reference the consensus sequence 208.

In one example and if desired, the compressed file 218 may be compressed with another compressor 220 (e.g., Hoffman Coding) to generate a compressed file 222, which has been compressed twice in this example. This allows the consensus sequence 208, which may be long, and/or the pointer pairs 216 to be compressed by the compressor 220 for additional space savings.

Figure 3:
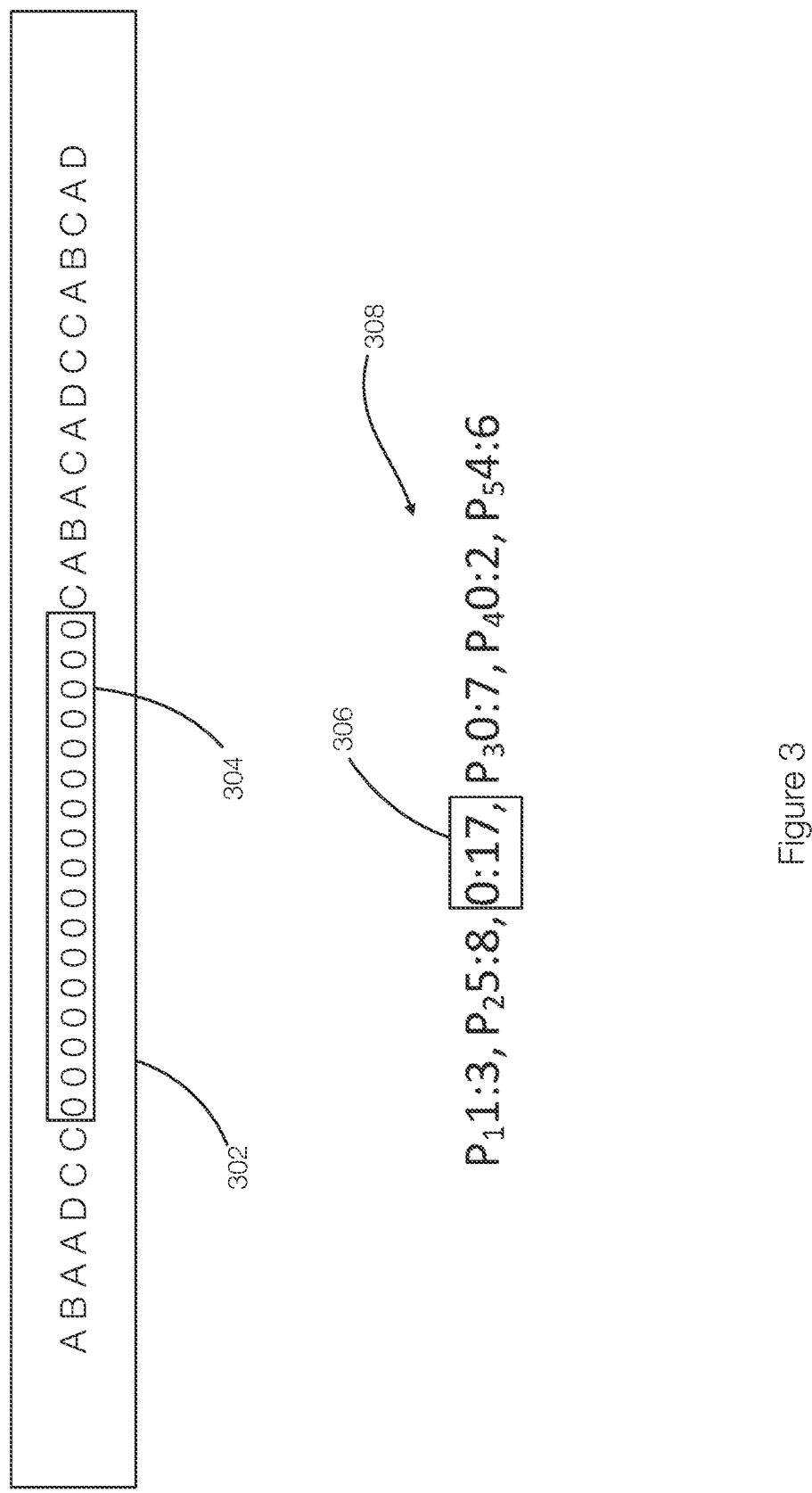
FIG. 3 discloses aspects of compressing data that include long zero sequences.

In one example, long 0 sequences (sequences of 0 bits) are not represented with a letter. Rather, long 0 sequences may be represented as a 0 sequence and a length. FIG. 3 discloses aspects of handling long 0 sequences in a file. FIG. 3 illustrates a file 302, which is similar to the file 202 but includes a zero sequence 304. In this example, sequencing the file 302 may result in the same matrix 206 as the zero sequence 304 may be omitted or handled differently. Thus, the pointer pairs for the file 304 are the same as discussed in FIG. 2.

In this example, the zero sequence 304 and its length are identified as a pair 306 and inserted into the pointer pairs 308 at the appropriate place (after $P_2$ and before $P_3$). The pair 306 represents a zero-sequence having a length of 17 bits—(0: 17). One sequences (a sequence of 1s) could be handled in a similar manner if present.

In one example, the actual data from the consensus sequence may be used in the pointer pairs instead of a pointer pair. More specifically, if the letters in the consensus sequence represent a small number of bits, it may conserve storage space to simply include the subsequence as present in the consensus matrix because the subsequence may take less space than the pointers (each pointer includes multiple bits).

Figure 4:
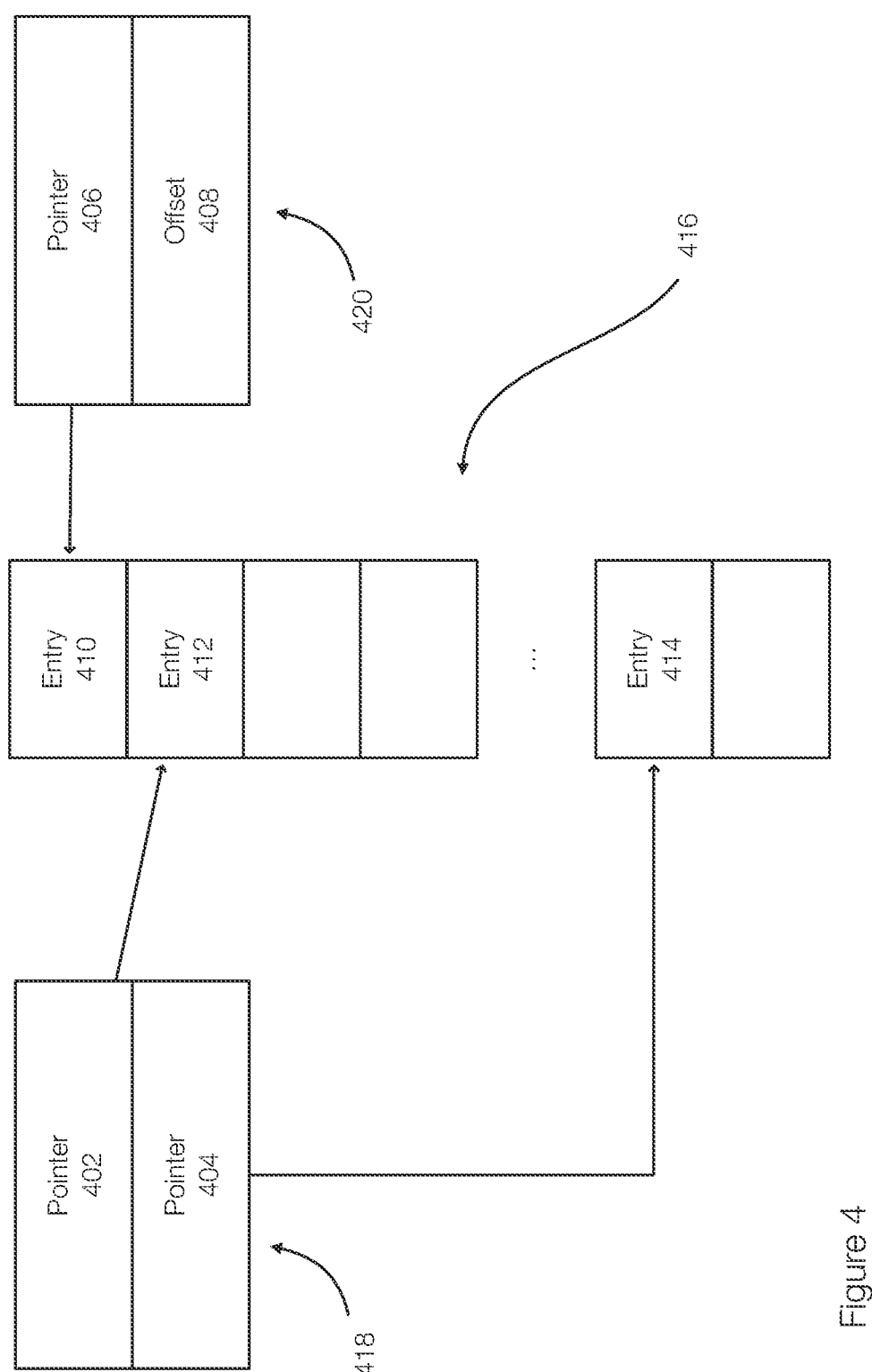
FIG. 4 discloses aspects of pointer pairs.

FIG. 4 discloses additional aspects of compressing data. FIG. 4 illustrates a consensus sequence 416, which includes various entries that may be represented as a vector. FIG. 4 illustrates a pointer pair 416, which includes pointer 402 and pointer 404. The pointer for points to entry 412 and the pointer 404 points to entry 414. The pointer pair 418 thus represents a portion of a file that has been compressed using a consensus sequence 416. The pointer pair 418 identifies a subsequence of the consensus sequence 416.

FIG. 4 also illustrates a pointer pair 406 that includes a pointer 406 and an offset 408. Using a pointer pair 406 may be useful and may conserve space by eliminating the need to store a second pointer (the offset may consume less space than a pointer). Thus, the pointer pair 420 identifies a starting entry 410 and an offset 408, which is the length of the subsequence identified by the pointer pair. Thus, the offset 408 may require less space than the pointer 404.

The length represented by the offset 408 may also be represented using a variable length quantity (VLQ) to conserve or manage storage requirements. For example, the length of the sequence represented by the offset 408 is less than 127, a single byte may be used. The most significant bit is used to identify whether other bytes are used to represent the length of the sequence. If the length is longer than 127, two bytes may be used as the offset.

Figure 5:
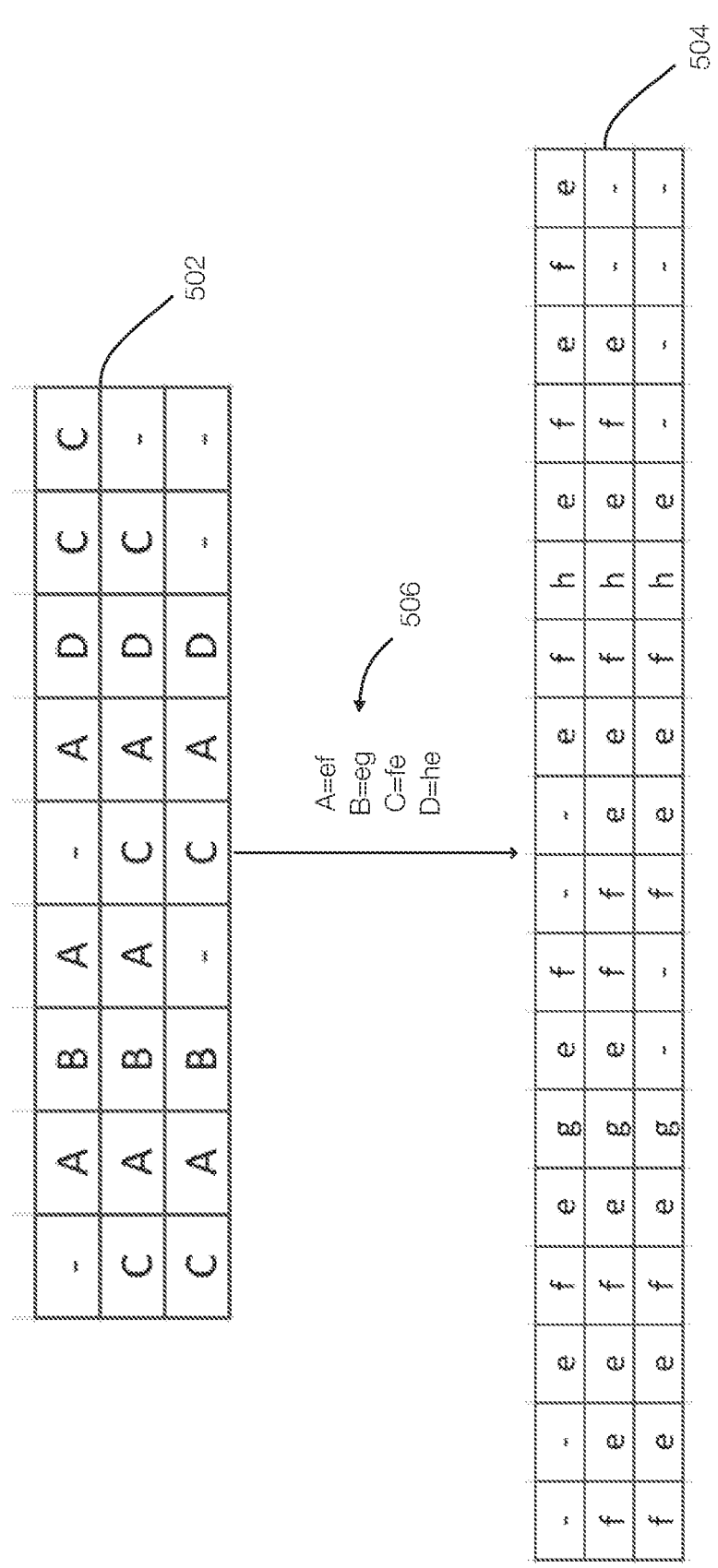
FIG. 5 discloses aspects of warming up operations to reduce computation times in compression operations.

FIG. 5 discloses aspects of warm starting a compression operation. The warm start, for example, may be used in alignments performed by the alignment operation (e.g., a greedy splitting operation). FIG. 5 illustrates a matrix 502, which is the same as the matrix 206. When the letter size is large (e.g., each letter represents 128 bits), the computation time to generate the matrix 502 and compress the input file may be faster compared to when the letter size is smaller. In this example, the matrix 502 resulted from processing a file.

Next, the letter sizes may be halved, thus the new letters 506 are generated as A=ef, B=eg, C=fe, and D=he. This may result in the matrix 504. More specifically, the matrix 502 (or the associated alignment) may be generated as larger letter sizes is associated with quicker computation times. Thus, the matrix 502 may be used as a prior for a subsequent alignment operation with iteratively reduced (e.g., halved) letter sizes. Thus, the matrix 502 (or alignment information generated by the alignment engine) is used as a starting point for generating the matrix 504.

Embodiments of the invention may also perform processing prior to aligning the file. For example, a size of a file may be large (e.g., terabytes). Compressing such a file may require significant amounts of RAM. As the letter size decreases or due to the size of the file or for other reasons, the available RAM may be insufficient. Embodiments of the invention may compress the file using hierarchical alignments.

Figure 6:
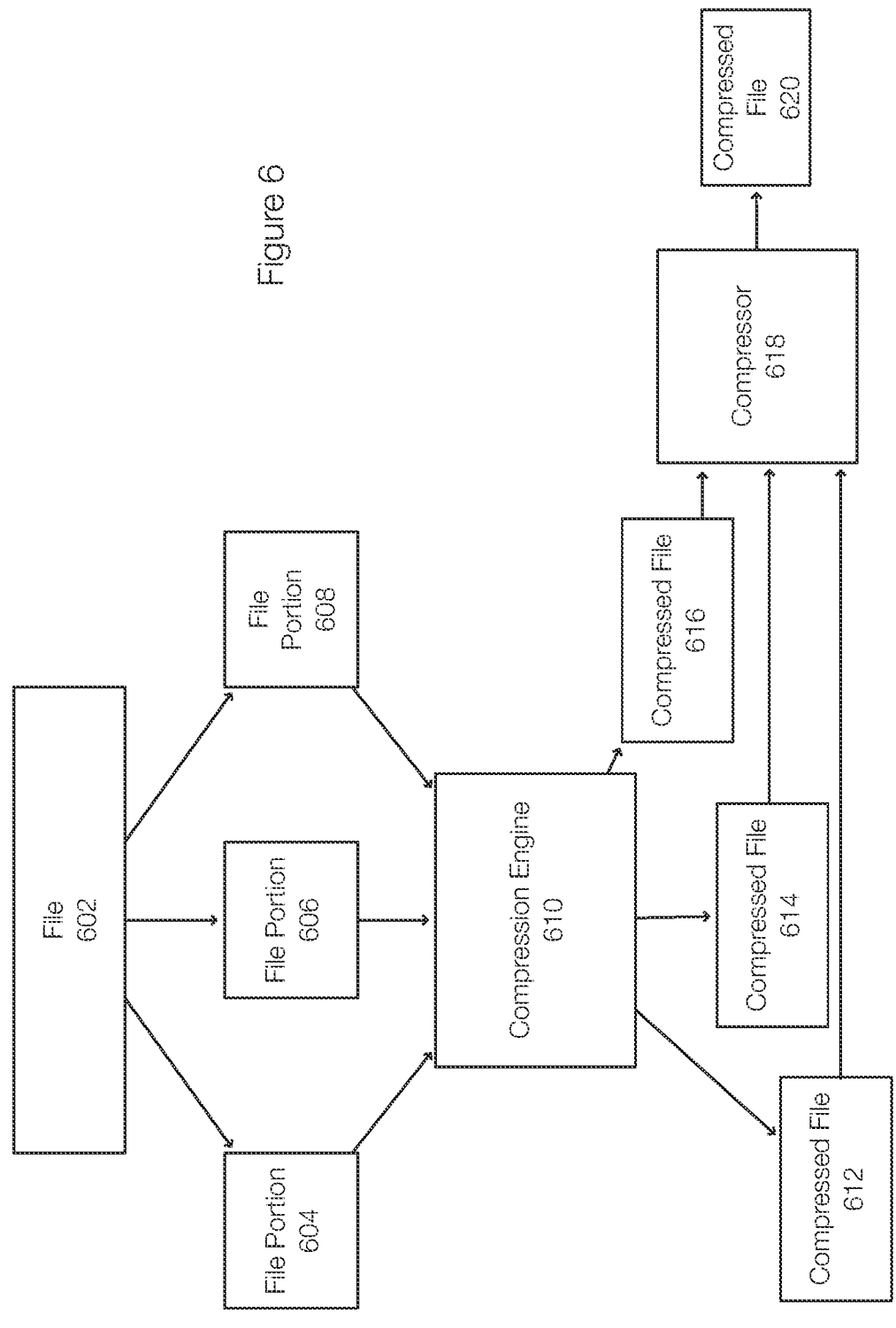
FIG. 6 discloses aspects of hierarchical compression.

FIG. 6 discloses aspects of hierarchical alignment. FIG. 6 illustrates a file 602 that may be large (e.g., terabytes). To accommodate existing resources, the file 602 may divided into one or more portions, illustrated as portions 604, 606, 608. These portions are then compressed (sequentially, concurrently, or using different compression engines) by the compression engine 610 to generate, respectively, compressed files 612, 614, and 616. A compressor 618, which may be difference from the compression engine 610 and use other compressors, may be used to compress the compressed files 612, 614, and 616 into a single compressed file 620. Thus, compresses files including a consensus sequence and pointer pairs are generated for each of the portions 604, 606, and 608 and these compressed files are either compressed or concatenated into the compressed file 620.

Figure 7:
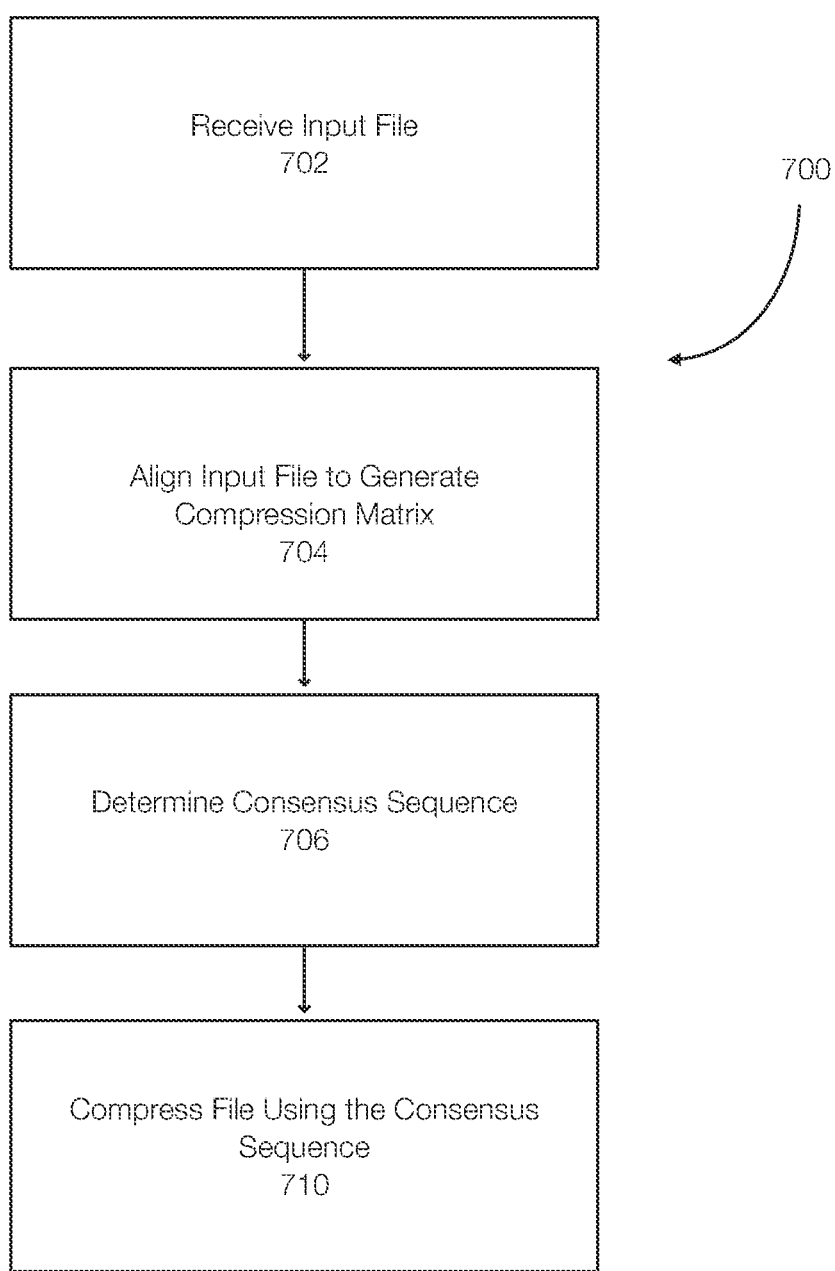
FIG. 7 discloses aspects of performing compression in a computing environment.

FIG. 7 discloses aspects of a method for compressing data. Initially, an input file is received 702 in the method 700 at a compression engine. The input file is then aligned 704 or sequenced by an alignment engine to generate a compression matrix. Aligning a file may include splitting the file one or more times and/or adding gaps as necessary in order to generate a plurality of sequences that are aligned. The sequences are aligned, for example, when the sequences generated by splitting the file can be arranged in a matrix such that each column includes a single letter and/or gaps.

Next, the consensus sequence is determined 706. This may be performed by flattening the matrix or by selecting, for each entry in the consensus sequence, the letter in the corresponding column of the compression matrix.

Once the consensus sequence is determined, the file is compressed 710. This may include generating pointer pairs that point to the consensus sequence. Each pointer corresponds to a portion of the file. The file can be decompressed or reconstructed by concatenating the portions of the consensus sequence (or bits corresponding to the letters in the consensus sequence) correspond to the pointer pairs.

The computational requirements to compress files as discussed herein can be reduced, at the cost of compression efficiency. Examples of hyperparameters or parameters to consider include letter size (number of bits), number of initial splits of a file, minimal consensus length reduction required by the alignment engine (e.g., splitting operation), the size of initial chunks, and the number of stages where consensus sequences are aligned to a larger consensus sequence. Additionally, the role of the file (e.g., data base Kubernetes cluster) and block size used by the operating systems.

Embodiments of the invention may be used for log storage. Many applications, including data science applications, generate or require log data. However, logs are often retained for a short period of time due to their size and the difficulty of storing many logs. In one example, these logs can be compressed as discussed herein to conserve storage space. Each log may be treated as a file. For logs with similar fields, the fields can be pre-aligned to provide a warm start. Further hierarchical alignments based on log characteristics can be considered. For example, first level logs generated by the same action may be aligned.

Compression as discussed herein can be applied to JSON (JavaScript Object Notation) like document storage and structured storages (e.g., SQL (Structured Query Language) Databases).

Embodiments of the invention may be used to compress text files. In this example, a text file is like a string and can be aligned with a letter size of a single letter. Real text files often contain patterns that can be aligned.

Image files may have a two-dimensional structure. Embodiments of the invention can be extended to two dimensions. In this case, each row of the matrix may have two dimensions and gaps may be present in each dimension. The alignment engine can operate in both axes. The pointers, which may include more than just pointer pairs in order to point to a polygon, point to corresponding polygons in the consensus image, which is a multi-dimensioned consensus matrix. Embodiments of the invention can be extended to additional dimensions. In this case, the pointer pairs are now pointer lists to corresponding polygon meshes.

Figure 8:
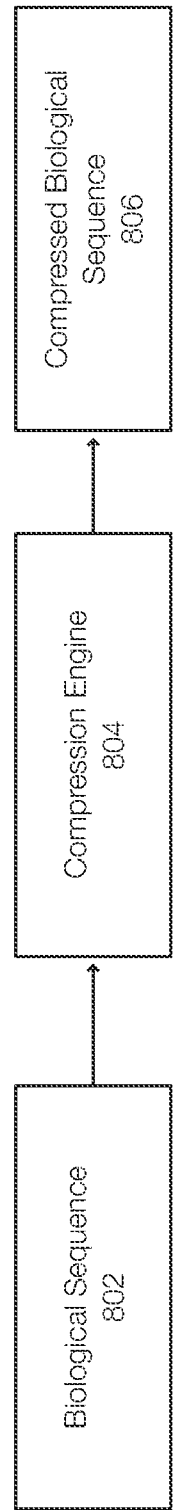
FIG. 8 discloses aspects of compressing biological sequences.

FIG. 8 discloses aspects of compressing biological sequences such as DNA (deoxyribonucleic acid) RNA (ribonucleic acid) sequences, protein sequences, nucleic sequences, and the like. Consider DNA sequences for example. It is generally accepted that there are four different types of DNA nucleotides: adenine (A), thymine (T), guanine (G), and cytosine (C). There are about 3.2 billion nucleotides in the human genome. In a simplistic example, if each nucleotide is represented as two bits, about 800 MB is required to store the DNA of a single person. The size is larger when considering that sequencing may include cut sequences from many genomes. This can substantially increase the amount of data associated with a sequencing process. It is anticipated that approximately 40 exabytes will be consumed by genomics projects in the next decade. The ability to compress DNA, RNA, protein, and other sequences can yield substantial memory savings.

Other biological sequences can be similarly represented. RNA can be represented using four bases—adenine (A), uracil (U), cytosine (C), and Guanine (G). Other biological sequences including other nucleic bases, protein sequences, or the like can be represented digitally and compressed as discussed herein.

DNA can be represented using four nucleotides and there may be many repetitions in a DNA string. Embodiments of the invention allow a biological sequence (e.g., a DNA sequence or a plurality of DNA sequences) to be compressed. When selecting a letter size, the letter may represent s string of nucleotides. For example, the letter size may represent 64 nucleotides. The letter size, however, may be larger or smaller.

The compression engine 804 is configured to compress the biological sequence 802 (or a plurality of biological sequences). In this example, the biological sequence may represent an entire DNA string of a species or a portion thereof.

The biological sequence 802 is aligned as described herein to generate a compression matrix. A consensus sequence is determined from the compression matrix and the biological sequence 802 is compressed into a compressed biological sequence 806.

When multiple biological sequences are being compressed, the files can be concatenated for splitting purposes. Alternatively, the biological sequences can be compressed hierarchically. In one example, each individual biological sequence can be compressed. The compressed biological sequences can be further compressed as illustrated in FIG. 6 by the compressor 618.

Figure 9:
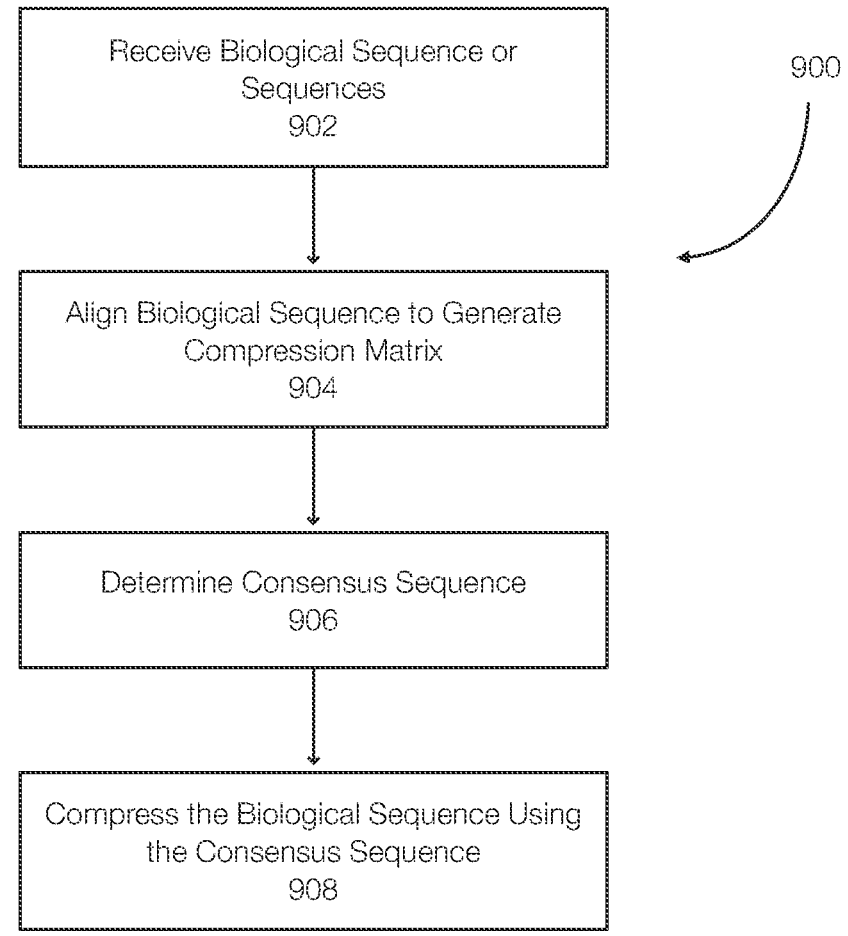
FIG. 9 discloses aspects of a method for compressing biological sequences.

FIG. 9 discloses aspects of compressing a biological sequence. Initially, a biological sequence or biological sequences are retrieved 902 in the method 900. The biological sequence(s) are aligned. This may include selecting a letter size or the like. Once the biological sequence(s) has been aligned and a compression matrix is generated, a consensus sequence is determined 906. The biological sequence is then compressed 908 using the consensus sequence and the compression matrix to generate a compressed biological sequence.

The DNA sequence (or other compressed file) can be decompressed by using the pointer pairs and the consensus sequence to, in effect, rebuild the biological sequence. The sequences in the compression matrix can be concatenated after gaps are removed to recover the original biological sequence.

In bioinformatics, multiple sequence alignment (MSA) may refer to a process or the result of sequence alignment of several biological sequences such as protein, DNA (deoxyribonucleic Acid), or RNA (ribonucleic acid). The input set of query sequences are assumed to have an evolutionary relationship. While the goal of MSA is to align the sequences, the output, in contrast to embodiments of the invention, may include multiple types of interactions including gaps, matches, and mismatches.

Appendix A includes an example of a Bacterial Foraging Optimization-Genetic Algorithm (BFO-GA) pseudocode and an example of an output of the BFO-GA algorithm. The BFO-GA, however, is not configured for compressing data, while embodiments of the invention relate to compressing data. Unlike BFO-GA and other MSA algorithms, the compression engine does not allow for mismatches and provides a positive score for subsequence matches above a certain length. Subsequence matches above a certain length facilitate the use of pointers during compression instead of the sequence itself.

The following is a discussion of aspects of example operating environments for various embodiments of the invention. This discussion is not intended to limit the scope of the invention, or the applicability of the embodiments, in any way.

In general, embodiments of the invention may be implemented in connection with systems, software, and components, that individually and/or collectively implement, and/ or cause the implementation of, compression operations and/or data protection operations. Data protection operations which may include, but are not limited to, data replication operations, IO replication operations, data read/write/delete operations, data deduplication operations, data backup operations, data restore operations, data cloning operations, data archiving operations, and disaster recovery operations.

More generally, the scope of the invention embraces any operating environment in which the disclosed concepts may be useful.

At least some embodiments of the invention provide for the implementation of the disclosed functionality in existing backup platforms, examples of which include the Dell-EMC NetWorker and Avamar platforms and associated backup software, and storage environments such as the Dell-EMC DataDomain storage environment. In general, however, the scope of the invention is not limited to any particular data backup platform or data storage environment.

New and/or modified data collected and/or generated in connection with some embodiments, may be stored in a data protection environment that may take the form of a public or private cloud storage environment, an on-premises storage environment, and hybrid storage environments that include public and private elements. Any of these example storage environments, may be partly, or completely, virtualized. The storage environment may comprise, or consist of, a data-center which is operable to service read, write, delete, backup, restore, and/or cloning, operations initiated by one or more clients or other elements of the operating environment. Where a backup comprises groups of data with different respective characteristics, that data may be allocated, and stored, to different respective targets in the storage environment, where the targets each correspond to a data group having one or more particular characteristics.

Example cloud computing environments, which may or may not be public, include storage environments that may provide data protection functionality for one or more clients. Another example of a cloud computing environment is one in which processing, data protection, and other, services may be performed on behalf of one or more clients. Some example cloud computing environments in connection with which embodiments of the invention may be employed include, but are not limited to, Microsoft Azure, Amazon AWS, Dell EMC Cloud Storage Services, and Google Cloud. More generally however, the scope of the invention is not limited to employment of any particular type or implementation of cloud computing environment.

In addition to the cloud environment, the operating environment may also include one or more clients that are capable of collecting, modifying, and creating, data. As such, a particular client may employ, or otherwise be associated with, one or more instances of each of one or more applications that perform such operations with respect to data. Such clients may comprise physical machines, virtual machines (VM), or containers.

Particularly, devices in the operating environment may take the form of software, physical machines, VMs, containers, or any combination of these, though no particular device implementation or configuration is required for any embodiment. Similarly, data protection system components such as databases, storage servers, storage volumes (LUNs), storage disks, replication services, backup servers, restore servers, backup clients, and restore clients, for example, may likewise take the form of software, physical machines, virtual machines (VM), or containers, though no particular component implementation is required for any embodiment.

As used herein, the terms 'data' and 'file' are intended to be broad in scope. Thus, these terms embrace, by way of example and not limitation, data segments such as may be produced by data stream segmentation processes, data chunks, data blocks, atomic data, emails, objects of any type, files of any type including media files, word processing files, spreadsheet files, and database files, as well as contacts, directories, sub-directories, volumes, images, logs, databases, multi-dimensional data, and any group of one or more of the foregoing.

It is noted that any of the disclosed processes, operations, methods, and/or any portion of any of these, may be performed in response to, as a result of, and/or based upon, the performance of any preceding process(es), methods, and/or, operations. Correspondingly, performance of one or more processes, for example, may be a predicate or trigger to subsequent performance of one or more additional processes, operations, and/or methods. Thus, for example, the various processes that may make up a method may be linked together or otherwise associated with each other by way of relations such as the examples just noted. Finally, and while it is not required, the individual processes that make up the various example methods disclosed herein are, in some embodiments, performed in the specific sequence recited in those examples. In other embodiments, the individual processes that make up a disclosed method may be performed in a sequence other than the specific sequence recited.

Following are some further example embodiments of the invention. These are presented only by way of example and are not intended to limit the scope of the invention in any way.

Embodiment 1. A method, comprising: receiving a biological sequence into a compression engine, aligning the biological sequence to create a compression matrix that includes sequences, wherein each of the sequences in the compression matrix corresponds to a portion of the biological sequence, determining a consensus sequence from the compression matrix, and generating a compressed biological sequence that includes the consensus sequence and pointer pairs, wherein each pointer pair identifies a subsequence of the consensus sequence.

Embodiment 2. The method of embodiment 1, wherein aligning the input file includes splitting the biological sequence a plurality of times.

Embodiment 3. The method of embodiment 1 and/or 2, wherein aligning the biological sequence includes determining a sequence length for the sequences.

Embodiment 4. The method of embodiment 1, 2, and/or 3, wherein aligning the biological sequence includes inserting gaps into at least some of the sequences.

Embodiment 5. The method of embodiment 1, 2, 3, and/or 4, wherein each pointer pair includes a first pointer and a second pointer that identify, respectively, starting and ending entries of a subsequence in the consensus sequence.

Embodiment 6. The method of embodiment 1, 2, 3, 4, and/or 5, wherein each pointer pair includes a first pointer to entry in the consensus sequence and a length of a subsequence starting from the entry.

Embodiment 7. The method of embodiment 1, 2, 3, 4, 5, and/or 6, wherein the biological sequence includes at least one of a DNA (deoxyribonucleic)sequence, an RNA (ribonucleic acid) sequence, a protein sequence, or a nucleic sequence.

Embodiment 8. The method of embodiment 1, 2, 3, 4, 5, 6, and/or 7, further comprising compressing the compressed biological sequence with a different compressor to generate a second compressed biological sequence.

Embodiment 9. The method of embodiment 1, 2, 3, 4, 5, 6, 7, and/or 8, wherein aligning the biological sequence comprises performing a multiple sequence alignment that is configured to disallow mismatches and that allows gaps.

Embodiment 10. The method of embodiment 1, 2, 3, 4, 5, 6, 7, 8, and/or 9, further comprising determining a letter size for aligning the biological sequence, wherein each letter corresponds to one or more nucleotides of the biological sequence.

Embodiment 11. A method comprising: retrieving a compressed biological sequence, identifying a consensus sequence and pointer pairs included in the compressed biological sequence, and decompressing the compressed biological sequence from the consensus sequence and the pointer pairs.

Embodiment 12. A method for performing any of the operations, methods, or processes, or any portion of any of these, or any combination thereof, disclosed herein.

Embodiment 13. A non-transitory storage medium having stored therein instructions that are executable by one or more hardware processors to perform operations comprising the operations of any one or more of embodiments 1-12.

The embodiments disclosed herein may include the use of a special purpose or general-purpose computer including various computer hardware or software modules, as discussed in greater detail below. A computer may include a processor and computer storage media carrying instructions that, when executed by the processor and/or caused to be executed by the processor, perform any one or more of the methods disclosed herein, or any part(s) of any method disclosed.

As indicated above, embodiments within the scope of the present invention also include computer storage media, which are physical media for carrying or having computer-executable instructions or data structures stored thereon. Such computer storage media may be any available physical media that may be accessed by a general purpose or special purpose computer.

By way of example, and not limitation, such computer storage media may comprise hardware storage such as solid state disk/device (SSD), RAM, ROM, EEPROM, CD-ROM, flash memory, phase-change memory ("PCM"), or other optical disk storage, magnetic disk storage or other magnetic storage devices, or any other hardware storage devices which may be used to store program code in the form of computer-executable instructions or data structures, which may be accessed and executed by a general-purpose or special-purpose computer system to implement the disclosed functionality of the invention. Combinations of the above should also be included within the scope of computer storage media. Such media are also examples of non-transitory storage media, and non-transitory storage media also embraces cloud-based storage systems and structures, although the scope of the invention is not limited to these examples of non-transitory storage media.

Computer-executable instructions comprise, for example, instructions and data which, when executed, cause a general-purpose computer, special purpose computer, or special purpose processing device to perform a certain function or group of functions. As such, some embodiments of the invention may be downloadable to one or more systems or devices, for example, from a website, mesh topology, or other source. As well, the scope of the invention embraces any hardware system or device that comprises an instance of an application that comprises the disclosed executable instructions.

Although the subject matter has been described in language specific to structural features and/or methodological acts, it is to be understood that the subject matter defined in the appended claims is not necessarily limited to the specific features or acts described above. Rather, the specific features and acts disclosed herein are disclosed as example forms of implementing the claims.

As used herein, the term 'module' or 'component' may refer to software objects or routines that execute on the computing system. The different components, modules, engines, and services described herein may be implemented as objects or processes that execute on the computing system, for example, as separate threads. While the system and methods described herein may be implemented in software, implementations in hardware or a combination of software and hardware are also possible and contemplated. In the present disclosure, a 'computing entity' may be any computing system as previously defined herein, or any module or combination of modules running on a computing system.

In at least some instances, a hardware processor is provided that is operable to carry out executable instructions for performing a method or process, such as the methods and processes disclosed herein. The hardware processor may or may not comprise an element of other hardware, such as the computing devices and systems disclosed herein.

In terms of computing environments, embodiments of the invention may be performed in client-server environments, whether network or local environments, or in any other suitable environment. Suitable operating environments for at least some embodiments of the invention include cloud computing environments where one or more of a client, server, or other machine may reside and operate in a cloud environment.

Figure 10:
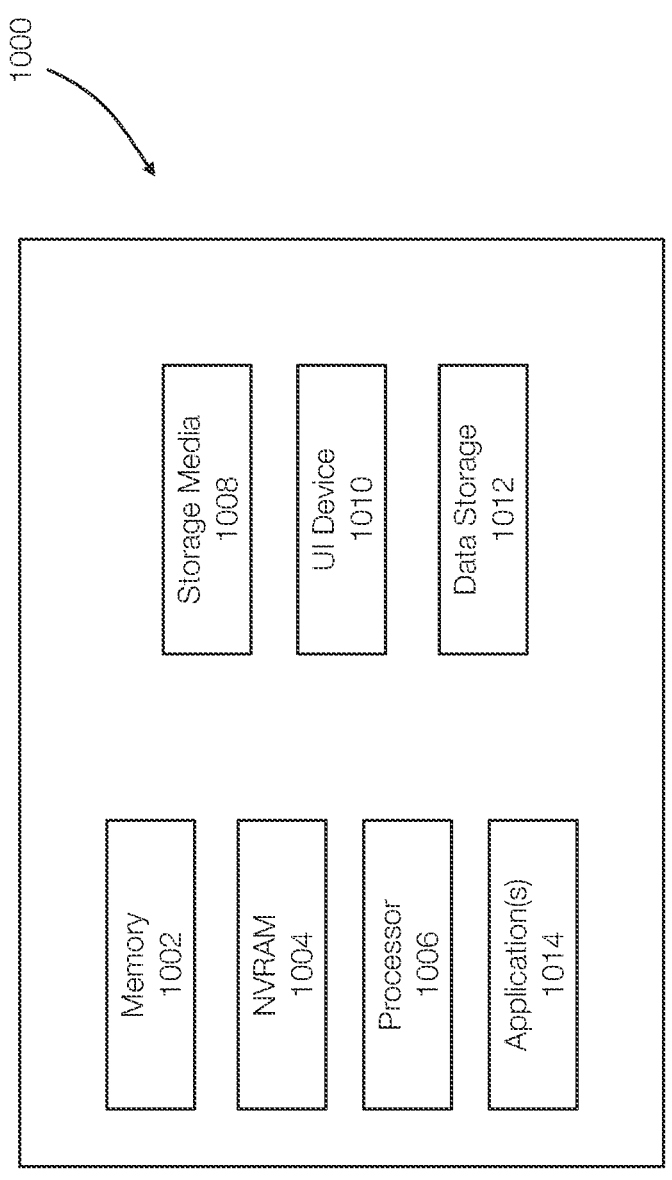
FIG. 10 discloses aspect of a computing device or a computing environment.

With reference briefly now to FIG. 10, any one or more of the entities disclosed, or implied, by Figures and/or elsewhere herein, may take the form of, or include, or be implemented on, or hosted by, a physical computing device, one example of which is denoted at 1000. As well, where any of the aforementioned elements comprise or consist of a virtual machine (VM), that VM may constitute a virtualization of any combination of the physical components disclosed in FIG. 10.

In the example of FIG. 10, the physical computing device 1000 includes a memory 1002 which may include one, some, or all, of random-access memory (RAM), non-volatile memory (NVM) 1004 such as NVRAM for example, read-only memory (ROM), and persistent memory, one or more hardware processors 1006, non-transitory storage media 1008, UI device 1010, and data storage 1012. One or more of the memory components 1002 of the physical computing device 1000 may take the form of solid-state device (SSD) storage. As well, one or more applications 1014 may be provided that comprise instructions executable by one or more hardware processors 1006 to perform any of the operations, or portions thereof, disclosed herein.

Such executable instructions may take various forms including, for example, instructions executable to perform any method or portion thereof disclosed herein, and/or executable by/at any of a storage site, whether on-premises at an enterprise, or a cloud computing site, client, datacenter, data protection site including a cloud storage site, or backup server, to perform any of the functions disclosed herein. As well, such instructions may be executable to perform any of the other operations and methods, and any portions thereof, disclosed herein.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method, comprising: receiving a biological sequence into a compression engine; aligning the biological sequence to create a compression matrix that includes sequences, wherein each of the sequences in the compression matrix corresponds to a different portion of the biological sequence and aligning the sequences includes inserting gaps into at least some of the sequences, wherein each row of the compression matrix includes one of the sequences and wherein each column of the compression matrix includes a same entry or a gap after the sequences are aligned, and wherein the aligning disallows mismatches; determining a consensus sequence derived from the compression matrix, the compression matrix being derived from the biological sequence, wherein the consensus sequence includes an entry from each of the columns and does not include any gaps; for each row of the compression matrix: generating one or more pointer pairs, wherein each pointer pair identifies a subsequence of entries in the row that does not include any gaps, wherein each pointer pair identifies a portion of the consensus sequence that corresponds to the subsequence of the row, wherein a first pointer in each of the pointer pairs for the row points to a different entry in the consensus sequence, and wherein the pointer pairs do not reference any gaps; and generating a compressed biological sequence from the biological sequence, wherein the compressed biological sequence includes the consensus sequence and the pointer pairs for all of the rows of the compression matrix.

2. The method of claim 1, wherein aligning the biological sequence includes splitting the biological sequence a plurality of times.

3. The method of claim 1, wherein aligning the biological sequence includes determining a sequence length for the sequences.

4. The method of claim 1, wherein each pointer pair includes the first pointer and a second pointer that identify, respectively, starting and ending entries of a subsequence in the consensus sequence.

5. The method of claim 1, wherein each pointer pair includes the first pointer to an entry in the consensus sequence and a length of a subsequence starting from the entry.

6. The method of claim 1, wherein the biological sequence includes at least one of a DNA (deoxyribonucleic) sequence, an RNA (ribonucleic acid) sequence, a protein sequence, or a nucleic sequence.

7. The method of claim 1, further comprising compressing the compressed biological sequence with a different compressor to generate a second compressed biological sequence.

8. The method of claim 1, wherein aligning the biological sequence comprises performing a multiple sequence alignment that is configured to disallow mismatches and that allows gaps.

9. The method of claim 1, further comprising determining a letter size for aligning the biological sequence, wherein each letter corresponds to one or more nucleotides of the biological sequence.

10. A non-transitory storage medium having stored therein instructions that are executable by one or more hardware processors to perform operations comprising: receiving a biological sequence into a compression engine; aligning the biological sequence to create a compression matrix that includes sequences, wherein each of the sequences in the compression matrix corresponds to a different portion of the biological sequence and aligning the sequences includes inserting gaps into at least some of the sequences, wherein each row of the compression matrix includes one of the sequences and wherein each column of the compression matrix includes a same entry or a gap after the sequences are aligned, and wherein the aligning disallows mismatches; determining a consensus sequence derived from the compression matrix, the compression matrix being derived from the biological sequence, wherein the consensus sequence includes an entry from each of the columns and does not include any gaps; for each row of the compression matrix: generating one or more pointer pairs, wherein each pointer pair identifies a subsequence of entries in the row that does not include any gaps, wherein each pointer pair identifies a portion of the consensus sequence that corresponds to the subsequence of the row, wherein a first pointer in each of the pointer pairs for the row points to a different entry in the consensus sequence, and wherein the pointer pairs do not reference any gaps; and generating a compressed biological sequence from the biological sequence, wherein the compressed biological sequence includes the consensus sequence and the pointer pairs for all of the rows of the compression matrix.

11. The non-transitory storage medium of claim 10, wherein aligning the biological sequence includes splitting the biological sequence a plurality of times.

12. The non-transitory storage medium of claim 10, wherein aligning the biological sequence includes determining a sequence length for the sequences.

13. The non-transitory storage medium of claim 10, wherein each pointer pair includes the first pointer and a second pointer that identify, respectively, starting and ending entries of a subsequence in the consensus sequence.

14. The non-transitory storage medium of claim 10, wherein each pointer pair includes the first pointer to an entry in the consensus sequence and a length of a subsequence starting from the entry.

15. The non-transitory storage medium of claim 10, wherein the biological sequence includes at least one of a DNA (deoxyribonucleic) sequence, an RNA (ribonucleic acid) sequence, a protein sequence, or a nucleic sequence.

16. The non-transitory storage medium of claim 10, further comprising compressing the compressed biological sequence with a different compressor to generate a second compressed biological sequence.

17. The non-transitory storage medium of claim 10, wherein aligning the biological sequence comprises performing a multiple sequence alignment that is configured to disallow mismatches and that allows gaps.

18. A method comprising: receiving a file into a compression engine; aligning the file to create a compression matrix that includes sequences, wherein each of the sequences in the compression matrix corresponds to a different portion of the file and aligning the sequences includes inserting gaps into at least some of the sequences, wherein each row of the compression matrix includes one of the sequences and wherein each column of the compression matrix includes a same entry or a gap after the sequences are aligned, and wherein the aligning disallows mismatches; determining a consensus sequence derived from the compression matrix, the compression matrix being derived from the biological sequence, wherein the consensus sequence includes an entry from each of the columns and does not include any gaps; for each row of the compression matrix: generating one or more pointer pairs, wherein each pointer pair identifies a subsequence of entries in the row that does not include any gaps, wherein each pointer pair identifies a portion of the consensus sequence that corresponds to the subsequence of the row, wherein a first pointer in each of the pointer pairs for the row points to a different entry in the consensus matrix sequence, and wherein the pointer pairs do not reference any gaps; and generating a compressed biological sequence from the biological sequence, wherein the compressed biological sequence includes the consensus sequence and the pointer pairs for all of the rows of the compression matrix, wherein the consensus sequence is stored with or separate from the pointer pairs.

19. The method of claim 18, wherein each pointer pair includes one of: the first pointer and a second pointer that identify, respectively, starting and ending entries of a subsequence in the consensus sequence; the first pointer to an entry in the consensus sequence and a length of a subsequence starting from the entry; a zero sequence; or a one sequence.

\* \* \* \* \*